United States Patent
Boehm (10) Patent No.: US 9,417,164 B2
(45) Date of Patent: Aug. 16, 2016

(54) MICROFLUIDIC ELEMENT FOR THOROUGHLY MIXING A LIQUID WITH A REAGENT

(71) Applicant: Roche Diagnostics Operations, Inc., Indianapolis, IN (US)

(72) Inventor: Christoph Boehm, Viernheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 619 days.

(21) Appl. No.: 13/803,747

(22) Filed: Mar. 14, 2013

(65) Prior Publication Data

US 2013/0196447 A1   Aug. 1, 2013

Related U.S. Application Data

(62) Division of application No. 12/330,583, filed on Dec. 9, 2008, now abandoned.

(30) Foreign Application Priority Data

Dec. 13, 2007 (EP) .................................. 07024210

(51) Int. Cl.
*G01N 1/38*  (2006.01)
*B01F 1/00*  (2006.01)
(Continued)

(52) U.S. Cl.
CPC ............. *G01N 1/38* (2013.01); *B01F 1/0022* (2013.01); *B01F 13/0059* (2013.01); *B01F 15/0201* (2013.01); *B01F 15/0233* (2013.01);
(Continued)

(58) Field of Classification Search
CPC ........ G01N 1/38; G01N 21/07; B01F 1/0022; B01F 13/0059; B01F 13/0064; B01F 15/0404; B01F 2005/0028; B01L 3/50273; B01L 3/502738; B01L 2300/087; B01L 2400/0409; B01L 2400/0688; B01L 2200/16; Y10T 436/25

See application file for complete search history.

(56) References Cited

U.S. PATENT DOCUMENTS

| 4,456,581 A | 6/1984 | Edelmann et al. |
| 4,580,896 A | 4/1986 | Brickus et al. |
| 4,814,144 A | 3/1989 | Edelmann et al. |
| 5,693,233 A | 12/1997 | Schembri |

(Continued)

FOREIGN PATENT DOCUMENTS

| EP | 0352690 A1 | 1/1990 |
| EP | 1077771 B1 | 7/1999 |
| WO | 95/33986 | 12/1995 |

OTHER PUBLICATIONS

Erickson, David et al. "Influence of Surface Heterogeneity on Electrokinetically Driven Microfuidic Mixing." Langmuir (2002) 18 1883-1892.

(Continued)

*Primary Examiner* — Christopher A Hixson
(74) *Attorney, Agent, or Firm* — Dinsmore & Shohl LLP (57) ABSTRACT

A microfluidic element for thoroughly mixing a liquid with a reagent used for the analysis of the liquid for an analyte contained therein and a method thereof are disclosed. The microfluidic element has a substrate and a channel structure. The channel structure includes an elongate mixing channel and an output channel. The mixing channel has an inlet opening and an outlet opening, and is implemented to mix the reagent contained therein with the liquid flowing through the inlet opening into the mixing channel. The outlet opening of the mixing channel is in fluid communication to the output channel. The outlet opening is positioned closer to the middle of the length of the mixing channel than the inlet opening.

22 Claims, 3 Drawing Sheets

(51) Int. Cl.
  *B01F 13/00* (2006.01)
  *B01F 15/02* (2006.01)
  *B01F 15/04* (2006.01)
  *B01L 3/00* (2006.01)
  *G01N 21/07* (2006.01)

(52) U.S. Cl.
  CPC ......... *B01F15/0404* (2013.01); *B01L 3/50273* (2013.01); *G01N 21/07* (2013.01); *B01L 2200/16* (2013.01); *B01L 2300/087* (2013.01); *B01L 2400/0409* (2013.01); *B01L 2400/0688* (2013.01); *Y10T 436/25* (2015.01)

(56) References Cited

U.S. PATENT DOCUMENTS

2002/0027133 A1  3/2002  Kellogg et al.
2004/0265171 A1  12/2004  Pugia et al.

OTHER PUBLICATIONS

Goldberg, Alfred L. "Protein Degradation and Protection Against Misfolded and Damaged Proteins." Nature (2003) 426 p. 895-899.

Handique, K. et al. "Nanoliter Liquid Metering in Microchannels Using Hydrophobic Patterns." Analytical Chemistry (2002) 72 p. 4100-4109.

Dertinger, et al., Generation of Gradients Having Complex Shapes Using Microfluidic Networks, Analytical Chemistry, vol. 73, No. 6, Mar. 15, 2001, pp. 1240-1246, USA.

MICROFLUIDIC ELEMENT FOR THOROUGHLY MIXING A LIQUID WITH A REAGENT

CROSS REFERENCE TO RELATED APPLICATIONS

This application is a divisional of U.S. patent application Ser. No. 12/330,583 filed Dec. 9, 2008 which claims priority to European Patent Application No. EP 07024210.2 filed Dec. 13, 2007.

FIELD OF THE INVENTION

The present invention relates generally to mixing structures, and in particularly to a microfluidic element for thoroughly mixing a liquid with a reagent and a method thereof.

BACKGROUND OF THE INVENTION

Microfluidic elements for thoroughly mixing a liquid with a reagent are used, for example, in diagnostic tests (in vitro diagnostics), using the microfluidic elements bodily fluid samples are analyzed for an analyte contained therein for medical purposes. The term thoroughly mixing comprises both the possibility that the reagent is provided in liquid form, i.e., that two liquids are mixed with one another, and also that the reagent is provided as a solid and is dissolved in a liquid and homogenized. An important component of the analysis is a so-called test carrier, on which, for example, microfluidic elements having channel structures for receiving a liquid sample (in particular a bodily fluid) are provided, to allow the performance of complex multistep test protocols. A test carrier can comprise one or more microfluidic elements.

For example, in immunochemical analyses having a multistep test sequence, in which a separation of bound and free reaction components occurs ("bound/free separation"), fluidic test carriers are used, using which a controlled liquid transport is possible. The control of the fluidic process sequence can be performed using internal measures (inside the fluidic element) or using external measures (e.g., provided in the device). The (external) control can be based on the application of pressure differentials or a change of forces, the latter being able to result from the change of the action direction of gravity, for example, but also from centrifugal forces which act on a rotating microfluidic element or a rotating test carrier and are a function of the rotational velocity and the distance from the axis of rotation, for example.

Microfluidic elements and also test carriers of this type comprise a carrier material, typically made of a substrate made of plastic material. The elements and test carriers have a sample analysis channel enclosed by the substrate and a cover or a cover layer, which often comprises a sequence of multiple channel sections and chambers lying between them, which are widened in comparison to the channel sections. The structures and dimensions of the sample analysis channel having its channel sections and chambers are defined by structuring of plastic parts of the substrate, which are generated, for example, by injection molding techniques or other methods for producing suitable structures.

To perform the analyses, the sample analysis channel contains a reagent which reacts with a liquid introduced into the sample analysis channel. The liquid sample and the reagent are mixed in the test carrier with one another in such a manner that a reaction of the sample liquid with the reagent results in a change of a measured variable which is characteristic for the analyte contained in the sample liquid. The measured variable is measured on the test carrier itself. Above all, optically analyzable measuring methods are typical, in which a color change or another optically measurable variable is detected.

Predominantly laminar flow conditions prevail in the sample analysis channel having its capillary channel structures and small dimensions. Liquids and/or liquids and solids mix thoroughly only poorly in such capillary channels. Multiple procedures are known in the prior art for improving the thorough mixing of reagent and sample liquid.

For example, in rotating test carriers which are rotated around a rotation axis in an analysis system, the thorough mixing is encouraged by rapid changes of the rotational direction or by changing the rotational velocity. This "shake mode" places high demands on the drive unit of the analysis system, however. The wear and the danger of occurring malfunctions and breakdowns are comparatively greater.

A further method known in the prior art for improving the thorough mixing of sample liquid and reagent is the introduction of magnetic particles which are set into motion by the action of an electromagnetic or permanent magnet. The outlay in the production of the test carrier rises due to the integration of the particles. In addition, the analysis systems must have a further component, namely the magnets.

Furthermore, elements are known whose capillary channels contain special flow obstructions, such as ribs. The production of obstructions of this type, which are often implemented as a microstructure, makes the production process of the test carrier more costly and difficult. In addition, structures of this type are not suitable for all mixing processes and/or for all reagents and sample liquids.

In spite of the many attempts to improve mixing procedures and microfluidic elements, such as test carriers, in particular the thorough mixing of reagent and sample liquid, there is a further need for a microfluidic element improved in this regard.

SUMMARY OF THE INVENTION

It is against the above background that the present invention provides embodiments which improve the thorough mixing of reagent and sample liquid.

In one embodiment, a microfluidic element for thoroughly mixing a liquid with a reagent used for analyzing the liquid for an analyte contained therein is disclosed. The microfluidic element comprises a cover layer, a substrate, and a channel structure enclosed by the substrate and the cover layer. The channel structure includes an elongate mixing channel and an output channel, wherein the mixing channel has an inlet opening and an outlet opening. The mixing channel is adapted for mixing the reagent contained therein with the liquid flowing through the inlet opening into the mixing channel, and wherein the outlet opening of the mixing channel is in fluid communication with the output channel, and the outlet opening is located closer to the middle of the length of the mixing channel than the inlet opening.

In another embodiment, a method for providing a homogeneous thoroughly mixed liquid is disclosed. The method comprises providing a microfluidic element having a substrate and a channel structure, wherein the channel structure includes an elongate mixing channel and an output channel. The mixing channel has an inlet opening and an outlet opening in fluid communication with the output channel, and wherein the outlet opening is located closer to the middle of the length of the mixing channel than the inlet opening. The method further comprises allowing a flow of liquid through the inlet opening into the mixing channel; dissolving a reagent contained in the mixing channel; exerting a force on the liquid in the mixing channel; and allowing the liquid to flow into the output channel through the outlet opening of the mixing channel so that thorough mixing of the liquid and the reagent occur.

These and other features and advantages of the present invention will become apparent after reading the detailed description of the various embodiments thereof in reference to the accompanying drawings.

BRIEF DESCRIPTION OF THE DRAWINGS

The present invention is illustrated by way of example and not with limitations in the accompanying figures, in which like references indicate similar elements, and in which.

DETAILED DISCUSSION

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. In addition, throughout the specification, and in the claims, the meaning of "a", "an", and "the" may include plural references. The meaning of "in" may include "in" and "on".

It is noted that recitations herein of a component of an embodiment being "adapted" or "configured" in a particular way or to embody a particular property, or function in a particular manner, are structural recitations as opposed to recitations of intended use. More specifically, the references herein to the manner in which a component is either "adapted" or "configured" denotes an existing physical condition of the component and, as such, is to be taken as a definite recitation of the structural characteristics of the component.

It is noted that terms like "generally," "commonly," and "typically," when utilized herein, are not utilized to limit the scope of the claimed embodiments or to imply that certain features are critical, essential, or even important to the structure or function of the claimed embodiments. Rather, these terms are merely intended to identify particular aspects of an embodiment or to emphasize alternative or additional features that may or may not be utilized in a particular embodiment.

For the purposes of describing and defining embodiments herein it is noted that the terms "substantially," "significantly," and "approximately" are utilized herein to represent the inherent degree of uncertainty that may be attributed to any quantitative comparison, value, measurement, or other representation. The terms "substantially," "significantly," and "approximately" are also utilized herein to represent the degree by which a quantitative representation may vary from a stated reference without resulting in a change in the basic function of the subject matter at issue.

The invention and its advantages are described and explained hereafter with reference in one embodiment to a test carrier for the analysis of a bodily fluid sample for an analyte contained therein without restriction of the generality of the microfluidic element.

The microfluidic element according to one embodiment is produced by appropriate structuring of a substrate, as described, for example, in M. Madou, *Fundamentals of Microfabrication*, CRC Press, Boca Raton, Fla., USA, 2002, the disclosure of which is herein incorporated fully by reference. The channel structure implemented in one embodiment as a channel includes an elongate mixing channel, which has an inlet opening and an outlet opening according to the invention and is implemented to mix a reagent contained therein with a liquid flowing through the inlet opening into the mixing channel. According to one embodiment, the mixing channel is in fluid communication with an output channel via the outlet opening.

In the meaning of the invention, a microfluidic element is understood in one embodiment as an element having a channel structure whose smallest dimension is greater than or equal to 5 µm and whose largest dimension (for example, length of the channel) is less than or equal to 10 cm.

An "elongate" channel is understood in the meaning of the application as a channel whose length is significantly greater than any cross-sectional dimension of its cross-sectional area. It is implied that the length is at least 10 times as large as the greater cross-sectional dimension in one embodiment. However, in another embodiment, the length of the channel is at least 20 times as large as the square root of the mean cross-sectional area of the channel. In still another embodiment, the length is at least 50 times and in still yet another embodiment, 100 times as great as the square root of the mean cross-sectional area. For a channel having a circular cross-sectional area, the length is in one embodiment 20 to 30 times as large as the radius.

It thus results for the dimensions that the largest cross-sectional dimension of a channel structure of a microfluidic element is at most in one embodiment 10 mm, and in another embodiment at most 5 mm. The largest cross-sectional dimension is more in one embodiment at most 2 mm, and in another embodiment at most 1 mm.

In the context of the invention, the fact is taken into consideration that a concentration gradient of the reagent arises within the mixing channel in the flow direction. Under conditions prevailing in microfluidic elements and/or test carriers, the concentration is normally least in the area of the inlet opening of the reagent and rises in the flow direction.

According to one embodiment of the invention, the outlet opening is positioned closer to the middle of the length of the mixing channel than the inlet opening. The mixing channel has a feed section between the inlet opening and the outlet opening and a complementary section downstream from the outlet opening (in the flow direction) and opposite to the inlet opening, wherein after the liquid flows into the mixing channel, the concentration of the reagent in the complementary section being different, typically higher, than the concentration in the feed section. The outlet opening is positioned on the length of the mixing channel so that the liquid flowing in the output channel through the outlet opening contains partial volumes from the feed section and the complementary section of the mixing channel in such a manner that the two liquid partial volumes are mixed in an accelerated way. The partial volumes (each flowing simultaneously through the outlet opening) from the feed section and from the complementary section have different concentrations of the reagent and are thoroughly mixed upon flowing into the output channel.

In other words, the microfluidic element is implemented in such a manner in one embodiment that the inlet opening of the mixing channel is positioned closer to one end of the mixing channel than the outlet opening. A liquid flowing through the inlet opening into the mixing channel of the channel (such as a bodily fluid sample) therefore flows from a position closer to the end of the mixing channel toward the outlet opening and thus toward a position closer to the middle of the length of the mixing channel.

The feed section of the mixing channel thus extends from a position closer to the end of the mixing channel to the outlet opening position closer to the middle of the length of the mixing channel. The complementary section is the part of the mixing channel between the outlet opening (more in the middle of the length) and the end of the mixing channel diametrically opposite to the inlet opening. During the supply into the output channel of the sample analysis channel, partial volumes flow simultaneously from both sections of the mixing channel through the outlet opening, the partial volumes of the particular section having different concentrations. Mixing of the liquid is encouraged in this way, so that a liquid having a homogeneous composition results rapidly. Through the output channel (possibly through further channel sections and/or channel chambers), the mixed liquid then reaches a zone in which the mixed liquid is processed further.

The microfluidic element according to another embodiment is part of a test carrier for the analysis of a bodily fluid sample for an analyte contained therein. The test carrier in one embodiment has a sample analysis channel enclosed by the substrate and a cover layer, which in one embodiment is the channel structure of the microfluidic element implemented as a channel. The term "substrate" is understood to mean that it is a carrier material in which the channel structure is introduced by structuring. For this purpose, methods for production and also materials typical to those skilled in the art are presumed, as are explained, for example, in the above-mentioned reference, M. Madou, *Fundamentals of Microfabrication*.

The sample analysis channel in one embodiment has a sample inlet opening (inlet opening) at its beginning. At its end, the sample analysis channel in one embodiment includes a measuring zone, which corresponds to the zone for further processing of the liquid in the microfluidic element. The liquid thoroughly mixed as it flows into the output channel reaches the measuring zone of the sample analysis channel through the output channel. In the measuring zone of the sample analysis channel a measured variable characteristic for the analyte is determined in one embodiment.

It is taken into consideration in the context of another embodiment of the invention that a higher concentration gradient occurs within the channel (sample analysis channel) if one or more dried, for example, lyophilized reagents are contained in the channel and are dissolved. Especially high concentration gradients arise in one embodiment upon the re-suspension of the dried reagents, because a liquid flowing into the mixing channel dissolves the dried reagents and they are washed further in the flow direction. In one embodiment, the reagents are already dissolved and transported further in the area of the inlet opening of the mixing channel upon entry of a liquid through the inlet opening, so that the concentration of the reagents or the reagent increases in the flow direction.

The element having its mixing channel with the inlet opening in one embodiment is positioned at one end of the channel and the outlet opening in one embodiment is positioned in the middle, which connects to the output channel in the mixing channel, is also capable of being used for other homogenization. For example, the mixing of two different solutions as is required for dilution, for example, is also improved hereby. The element and/or the test carrier is thus not only restricted to dry reagents, but rather can also be employed for mixing two liquids, in particular reagents provided in liquid form.

The element according to various embodiments of the invention such as, for example, the test carrier, has the following noted advantages, but not limited thereto. The production costs of the element or test carrier are practically not increased by the mixing apparatus, because microstructures, such as ribs or additional constrictions, are dispensed with. The analysis device, with which the test carrier forms an analysis system, does not require any special design. In particular, for rotating analysis systems, no additional outlay is required for the drive (as for systems using the shaking method, for example). The production costs of the device are therefore also low. Additional substances, such as magnetic particles (magnet beads), which have to be introduced into the test carrier, are not necessary. The analyses are therefore cost-effective and the (partially manual) effort is low. Finally, the element is also suitable for thoroughly mixing solutions having a large concentration gradient.

In one embodiment, the microfluidic element is rotatable around an axis of rotation. The axis of rotation in one embodiment extends through the element. Test carriers or microfluidic elements which rotate around their center are especially suitable.

In another embodiment of the microfluidic element, a capillary stop is positioned in the element, which forms a flow resistance for liquid flowing from the mixing channel into the output channel in such a manner that spontaneous emptying of the mixing channel into the output channel is prevented until the flow resistance is overcome by an external force. This prevents liquid from entering the output channel through the outlet opening from the mixing channel solely because of the capillary effect. The capillary stop is in one embodiment positioned directly after the outlet opening of the mixing channel.

The external force which is necessary for overcoming the flow resistance in one embodiment is a centrifugal force which is generated by rotation of the microfluidic element. The centrifugal force and thus the reaction process and/or the thorough mixing process can be controlled by suitable selection of the rotational velocity or by change of the rotational velocity, for example, the dwell time of a liquid in the mixing channel can be controlled.

The external force is also in one embodiment a pressure force which acts on the liquid in the mixing channel. For example, the pressure force can be implemented by generating an overpressure or a partial vacuum within the test carrier.

The capillary stop in one embodiment has a channel section which includes at least one hydrophobic channel wall. The channel wall in one embodiment is made hydrophobic using a hydrophobizing substance. A hydrophobic channel capillary block of this type also prevents the independent flow through the channel section of this channel.

An exemplary embodiment of a microfluidic element is described hereafter on the basis of a test carrier (without restriction of the generality) and on the basis of the drawings. The technical features shown therein may be used individually or in combination to provide other embodiments of the invention. They do not represent any restriction of the generality.

Figure 1:
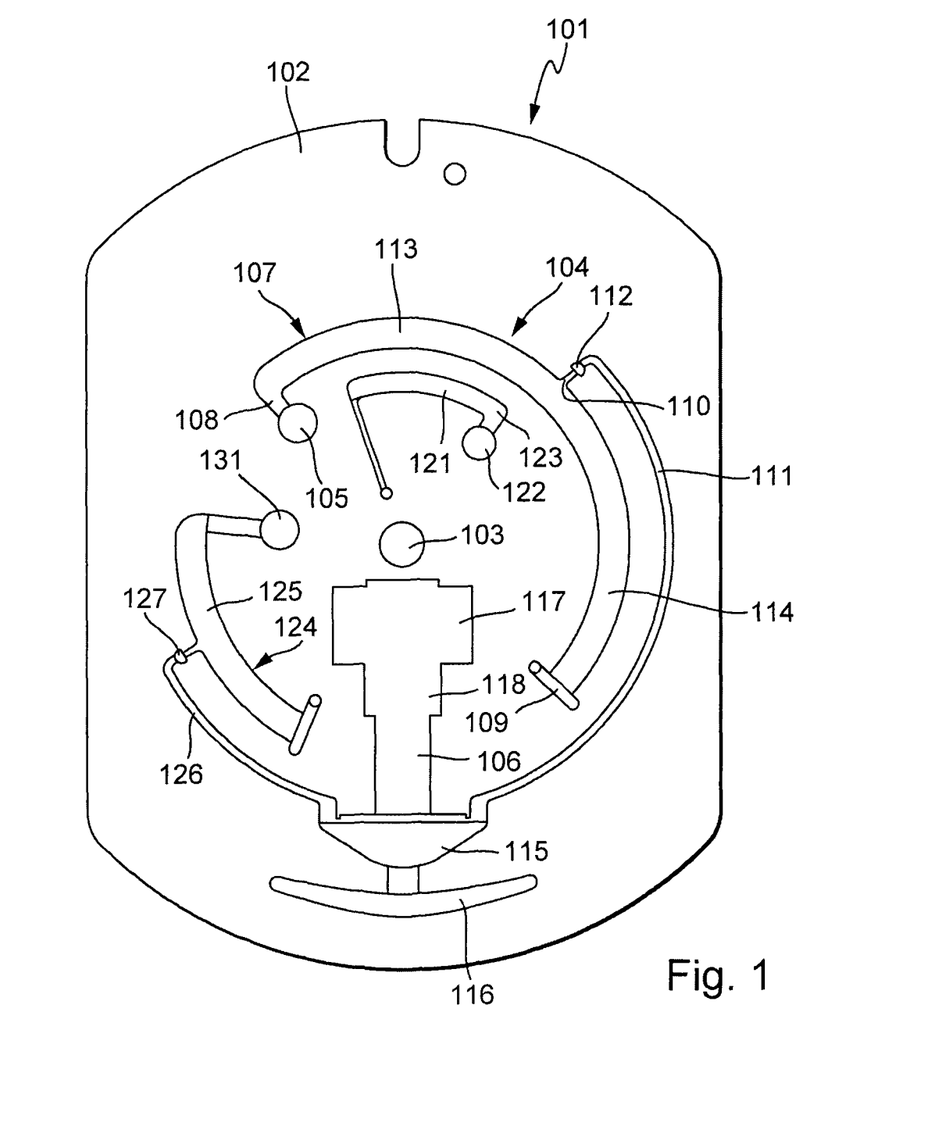
FIG. 1 shows a test carrier having a sample analysis channel and a mixing channel.

FIG. 1 shows a test carrier 101 according to the invention having a substrate 102 and a hole 103 in the center of the test carrier 101, through which an axis of rotation extends, around which the disc-shaped test carrier 101 rotates.

A sample analysis channel 104 includes a sample inlet opening 105 at its beginning, through which a liquid sample, which in one embodiment is blood, for example, can be introduced into the sample analysis channel 104. For example, a sample liquid can be dispensed by a user manually (using a pipette) into the sample inlet opening 105. Alternatively, a sample can be dosed by a dosing station of an analysis device through the sample inlet opening 105 into the sample analysis channel 104. At its end, the sample analysis channel 104 enclosed by the substrate 102 includes a measuring zone 106, in which a measured variable characteristic for an analyte in the sample liquid is detected, and in one embodiment also optically measured.

The sample analysis channel 104 includes a mixing channel 107, in which a reagent is contained in dried form, in one embodiment in lyophilized form. The dried reagent is dissolved by the inflowing liquid in the mixing channel 107.

The mixing channel 107 has an inlet opening 108, which has a fluid connection to the sample inlet opening 105, at one end (beginning). At its other end, a barrier 109 is provided, which is implemented as a geometric valve, and is used to ventilate the mixing channel.

An outlet opening 110 is positioned in the middle of the length of the mixing channel 107, via which the mixing channel 107 has a fluid connection to an output channel 111. A capillary stop 112, which is implemented as a geometric valve, is positioned between the outlet opening 110 and the output channel 111. It is shown in detail in FIG. 2. The capillary stop 112 prevents a liquid contained in the mixing channel 107 from flowing automatically (self-acting) into the output channel 111. The capillary forces acting on the liquid in the channels 107, 111 are insufficient to overcome the capillary stop 112. This ensures that the mixing channel 107 can be filled by a defined sample volume. The flow resistance of the capillary flow 112 is first overcome when the rotational velocity, at which the test carrier 101 is rotated, generates a sufficiently great centrifugal force, which acts on the liquid in the mixing channel 107. The action (action time) of the sample liquid on the reagent contained in the mixing channel 107 can thus be controlled.

The mixing channel 107 in one embodiment has a rectangular cross-section. In case of a rotating test carrier 101, the mixing channel 107 is implemented in such a manner that the greater cross-sectional dimension extends in a plane of rotation running perpendicularly to the axis of rotation. The other channels, in particular the output channel 111, are in one embodiment also implemented as rectangular. They thus have a rectangular cross-section. Channels or channel structures of this type are very simple and cost-effective to produce.

The mixing channel 107 shown in this exemplary embodiment forms a semicircle, which extends at a constant radius around the axis of rotation (hole 103) of the test carrier 101. The inlet opening 108 and the outlet opening 110 of the mixing channel 107 are, as shown here, in one embodiment positioned in such a manner that the distance of the outlet opening 110 from the axis of rotation is greater than the distance of the inlet opening 108 from the axis of rotation. This has the advantage that the mixing channel 107 can be emptied completely. The entire volume flowing into the mixing channel 107 can be conducted to the measuring zone 106 and is available for the analysis of the sample liquid. Of course, another configuration of the mixing channel 107 is also possible. For rotating test carriers 101, the distance of the outlet opening from the axis of rotation is in one embodiment always to be greater than the distance of the inlet opening, so that the liquid is pressed out of the outlet opening 110 by the centrifugal forces arising upon the rotation.

The mixing channel 107 includes a feed section 113 between the inlet opening 108 and the outlet opening 110 and a complementary section 114 between the outlet opening 110 and the barrier 109 at the end of the mixing channel 107. When a sample liquid flows through the inlet opening 108 into the mixing channel 107, the reagent contained in the mixing channel 107 is dissolved. The dissolved parts of the sample liquid are transported in the flow direction through the mixing channel 107. A concentration gradient results in the mixing channel 107 through the further transport of the dissolved reagent parts, wherein a lower concentration of the reagent exists in the feed section 113 than in the complementary section 114. The concentration in the mixing channel 107 is greatest in the area of the barrier 109, and lowest at the inlet opening 108.

In general, only poor thorough mixing occurs in the mixing channel 107 because of the capillary flow conditions. Upon reaching a suitable rotational velocity, at which the flow resistance of the capillary stop 112 is overcome by the sample liquid, however, partial volumes flow from the feed section 113 and from the complementary section 114 through the outlet opening 110 into the output channel 111. The individual partial volumes are thoroughly mixed in the output channel 111 rapidly, so that a homogeneous composition arises.

Figure 3A:
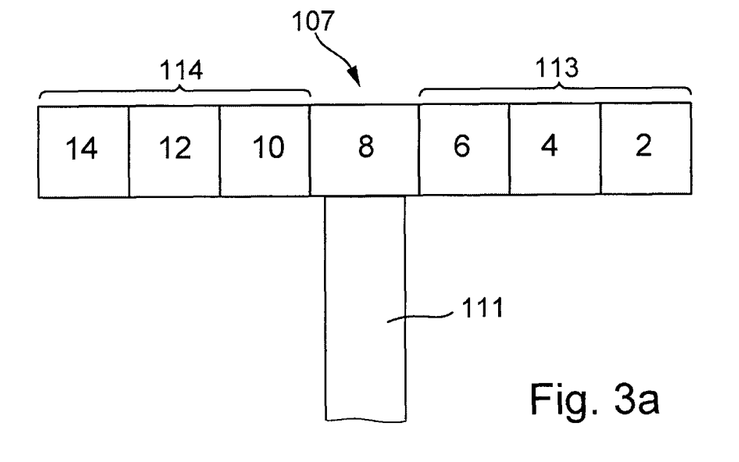
FIGS. 3a and 3b show a schematic outline to explain the thorough mixing achieved using the invention.
Figure 3B:
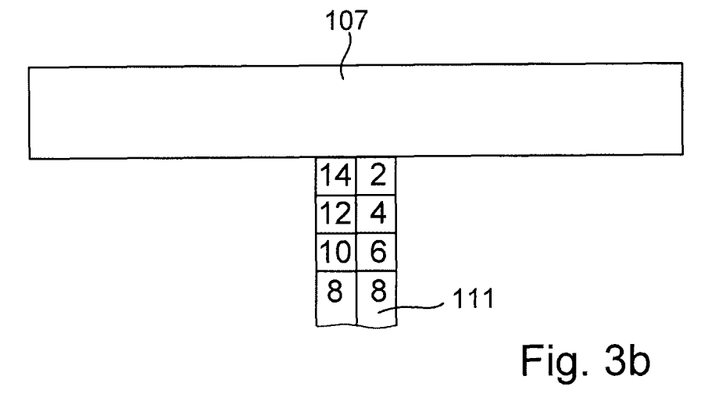

The procedure of the thorough mixing is shown in FIGS. 3a and 3b on the basis of a schematic outline, which shows the mixing channel 107 and the output channel 111 (without capillary stop 112). The concentration of the reagent in the mixing channel 107 is schematically shown on the basis of symbolic concentration values 2 through 14 (in arbitrary units). Of course, in practice the concentration distribution in the mixing channel is not discrete as shown in the outline here. Typically, a continuous, not necessarily linear distribution is formed.

After a liquid has flowed into the mixing channel 107 and the reagent is dissolved, a concentration distribution shown in FIG. 3a results. The concentration in the mixing channel 107 is less in the feed section 113 than in the complementary section 114. The concentration is lowest at the right end in FIG. 3, and greatest at the left end in FIG. 3. Partial volumes flow from the feed section 113 and the complementary section 114 into the output channel 111 from the filled mixing channel. As shown in FIG. 3b, the flow paths resulting in the output channel 111 from the individual sections 113, 114 supplement one another mutually (ideally complementary) to one another in such a manner that an optimized and very uniform thorough mixing of the sample liquid with the reagent occurs.

It has been shown in the context of the invention that optimum mixing results are achieved by positioning the inlet opening 108 at one end of the mixing channel 107 and positioning the outlet opening 110 in the middle of the mixing channel 107. Slight variations of the optimum positioning of the two openings 108, 110 do not result in significant impairment of the mixing results. In one embodiment, the outlet opening 110 is positioned in such a manner that it is positioned at most 20% of the length of the mixing channel 107 distant from the middle of the length of the mixing channel 107. In another embodiment, the inlet opening 108 is at most 20% of the length of the mixing channel 107 distant from one end of the mixing channel 107. If the openings 108, 110 are positioned within the above mentioned tolerance width, very good mixing results are achieved. The influence on the mixing results in comparison to the optimum result is negligible for a distance from the optimum location up to at most 5%.

At suitable rotational velocities, a separation of red blood cells and other cellular sample components already occurs in the output channel 111. The thoroughly mixed liquid, comprising sample liquid and reagent dissolved therein, is conducted at suitable rotational velocities into a collection chamber 115 (plasma collection chamber) and a collection chamber 116 (erythrocyte collection chamber). The red blood cells collect in the collection chamber 116 due to the acting centrifugal forces, while the blood plasma essentially remains in the collection chamber 115.

The measuring zone 106 is in one embodiment implemented as a porous, absorbent matrix. If the rotation of the test carrier is stopped or slowed, the reagent-sample mixture is absorbed (suctioned) into the measuring zone 106. A waste chamber 117 is positioned behind the measuring zone 106 in the flow direction, in which the reaction participants, sample and/or reagent components, are disposed of after flowing through the measuring zone 106.

The test carrier 101 of the exemplary embodiment shown also has a priming structure 121, which includes a flushing liquid opening 122 and a flushing liquid collection chamber 123.

The test carrier 101 has a second channel 124 having a inlet opening 131. The channel 124 essentially corresponds in its structure to the sample analysis channel 104. However, it describes a quarter circle in contrast to the sample analysis channel 104. The second channel 124, which can also be a sample analysis channel, includes a mixing channel 125, an output channel 126, and a capillary stop 127 positioned between them. Its length, at approximately 25 to 30 mm, is approximately half of the length of the sample analysis channel 104 (55-65 mm). The width of the two channels 104, 124 is 3 mm each, while the depth (dimension in the axial direction of the axis of rotation) is approximately 0.15 mm.

The channel 124, which is also in fluid communication with the collection chamber 115, is used in particular to receive a further liquid, in particular a buffer solution, which is required for the analysis, for example, for the bound/free separation. A reagent is in one embodiment contained in the mixing channel 125, which is used for the analysis of the sample liquid analyzed in the measuring zone. Alternatively, a further (different) sample and/or a (different) reagent can also be thoroughly mixed with the sample in the channel 124. The thoroughly mixed liquid is then conducted to the measuring zone 106.

Figure 2:
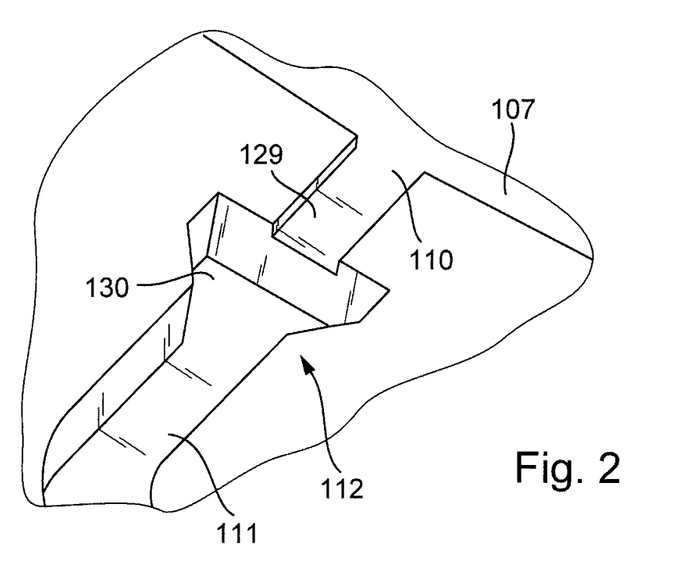
FIG. 2 shows a detail illustration of a capillary stop at an outlet opening of the mixing channel from FIG. 1.

FIG. 2 shows the capillary stop 112 in detail. The capillary stop 112 is formed by a geometric valve 128, which includes a primary section 129 and a secondary section 130, which adjoins the primary section 129 in the flow direction. The cross-sectional area of the primary section 129 adjoining the outlet opening 110 is less than the cross-sectional area of the secondary section 130.

With a rectangular cross-sectional area of the capillary channels, the primary section 129 of the capillary stop 112 is also rectangular; it thus also has a rectangular cross-sectional area, as does the secondary section 130. The cross-sectional dimension of the primary section 129 in the axial direction of the axis of rotation is in one embodiment less than the corresponding cross-sectional dimension of the secondary section 130. The cross-sectional dimension of the primary section 129 in the direction transverse to the axis of rotation is also less than the corresponding cross-sectional dimension of the secondary section 130. The flow resistance of the geometric valve 128 can be set by a suitable selection of the dimensions of the primary section 129 and the secondary section 130.

The required centrifugal force and thus the rotational velocity of the test carrier 101 which is necessary so that a liquid can flow through the capillary stop 112 are thus established.

The foregoing exemplary descriptions and the illustrative preferred embodiments of the present invention have been explained in the drawings and described in detail, with varying modifications and alternative embodiments being taught.

While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A method for providing a homogeneous thoroughly mixed liquid comprising:
   providing a microfluidic element having a substrate and a channel structure, wherein the channel structure includes an elongate mixing channel and an output channel, wherein the mixing channel has a directly adjoining inlet opening and an outlet opening, the outlet opening being in fluid communication with the output channel, wherein the outlet opening is located closer to the middle of the length of the mixing channel than the inlet opening, and, wherein the mixing channel has a feed section between the inlet opening and the outlet opening and a complementary section, downstream from the outlet opening in the flow direction and opposite to the inlet opening;
   receiving in the mixing channel a flow of liquid exteriorly applied directly to the inlet opening;
   dissolving a reagent contained in the mixing channel; and
   exerting a force on the liquid in the mixing channel to:
   allow the liquid to flow into the output channel through the outlet opening of the mixing channel so that thorough mixing of the liquid and the reagent occur, and
   flow partial volumes from the feed section and the complementary section of the mixing channel through the outlet opening into the output channel such that mixing of the two liquid partial volumes is supported by exertion of the force on the liquid.

2. The method according to claim 1, wherein the microfluidic element further comprises a cover layer.

3. The method according to claim 2, wherein the channel structure is enclosed by the substrate and cover layer.

4. The method according to claim 1, wherein the exerted force is a centrifugal force which is generated by rotating the microfluidic element.

5. The method according to claim 1, wherein the microfluidic element is a test carrier.

6. The method according to claim 5, wherein the test carrier comprises a second channel in fluid communication with a collection chamber, wherein the second channel includes an inlet opening, a mixing channel, an output channel, and a capillary stop positioned between them, the method further comprising receiving an additional liquid.

7. The method according to claim 6, wherein the additional liquid is a buffer solution.

8. The method according to claim 6, wherein the second channel is a sample analysis channel.

9. The method according to claim 3, wherein the channel structure is a sample analysis channel which comprises a sample inlet opening and a measuring zone.

10. The method according to claim 9, further comprising allowing the liquid to flow into the measuring zone and determining a measured variable characteristic for an analyte.

11. The method according to claim 10, wherein the analyte is detected optically.

12. The method according to claim 1, wherein the exerted force is a pressure force which is implemented by generating an overpressure or partial vacuum within the carrier.

13. The method according to claim 1, wherein the reagent is in dried form.

14. The method according to claim 13, wherein the reagent is in lyophilized form.

15. The method according to claim 1, wherein the microfluidic element further comprises a capillary stop which forms a flow resistance for the liquid flowing from the mixing channel into the output channel in such a manner that spontaneous emptying of the mixing channel into the output channel is prevented until the flow resistance is overcome by an external force.

16. The method according to claim 1, wherein the concentration in the liquid partial volume from the feed section and the concentration in the liquid partial volume from the complementary section supplement one another mutually or complementary such that an uniform thorough mixing occurs upon entrance in the output channel.

17. The method according to claim 1, wherein a thorough mixing occurs upon entrance in the output channel and wherein the concentration in the liquid partial volume in the feed section differs from the concentration in the liquid partial volume in the complementary section.

18. The method according to claim 1, wherein upon flowing into the output channel the amount of the liquid partial volume from the feed section equals the amount of the liquid partial volume of the complementary section such that a homogenous mixing is effected.

19. The method according to claim 1, wherein the outlet opening is positioned at most 20% of the length of the mixing channel distant from the middle of the length of the mixing channel.

20. The method according to claim 1, wherein the inlet opening is at most 20% of the length of the mixing channel distant from one end of the mixing channel.

21. The method according to claim 4, wherein the channel structure comprises a collection chamber connected to the outlet channel and a measurement zone connected to the collection chamber, and the method further comprises stopping or slowing the rotating of the microfluidic element to draw the fluid into the measuring zone from the collection chamber.

22. A method for providing a homogeneous thoroughly mixed liquid comprising:
providing a microfluidic element having a substrate and a channel structure, wherein the channel structure includes an elongate mixing channel and an output channel, wherein the mixing channel has a directly adjoining inlet opening and an outlet opening in fluid communication with the output channel, wherein the outlet opening is located closer to the middle of the length of the mixing channel than the inlet opening, and, wherein the mixing channel has a feed section between the inlet opening and the outlet opening and a complementary section, downstream from the outlet opening in the flow direction and opposite to the inlet opening;
receiving in the mixing channel a flow of liquid exteriorly applied directly to the inlet opening, in which said liquid self fills the mixing channel via capillary action and dissolves a reagent contained in the mixing channel; and
directly following the receiving in the mixing channel the flow of liquid, exerting a force on the liquid in the mixing channel necessary to overcome flow resistance to the output channel, wherein said force causes partial volumes of the liquid to simultaneously flow from the feed section and the complementary section of the mixing channel through the outlet opening into the output channel which results in thorough mixing of the liquid and the dissolved reagent via the mixing of the two liquid partial volumes that is supported by exertion of the force on the liquid.

* * * * *